Feb. 13, 1973 D. L. ARMSTRONG Plant Pat. 3,302
ROSE PLANT
Filed April 15, 1971
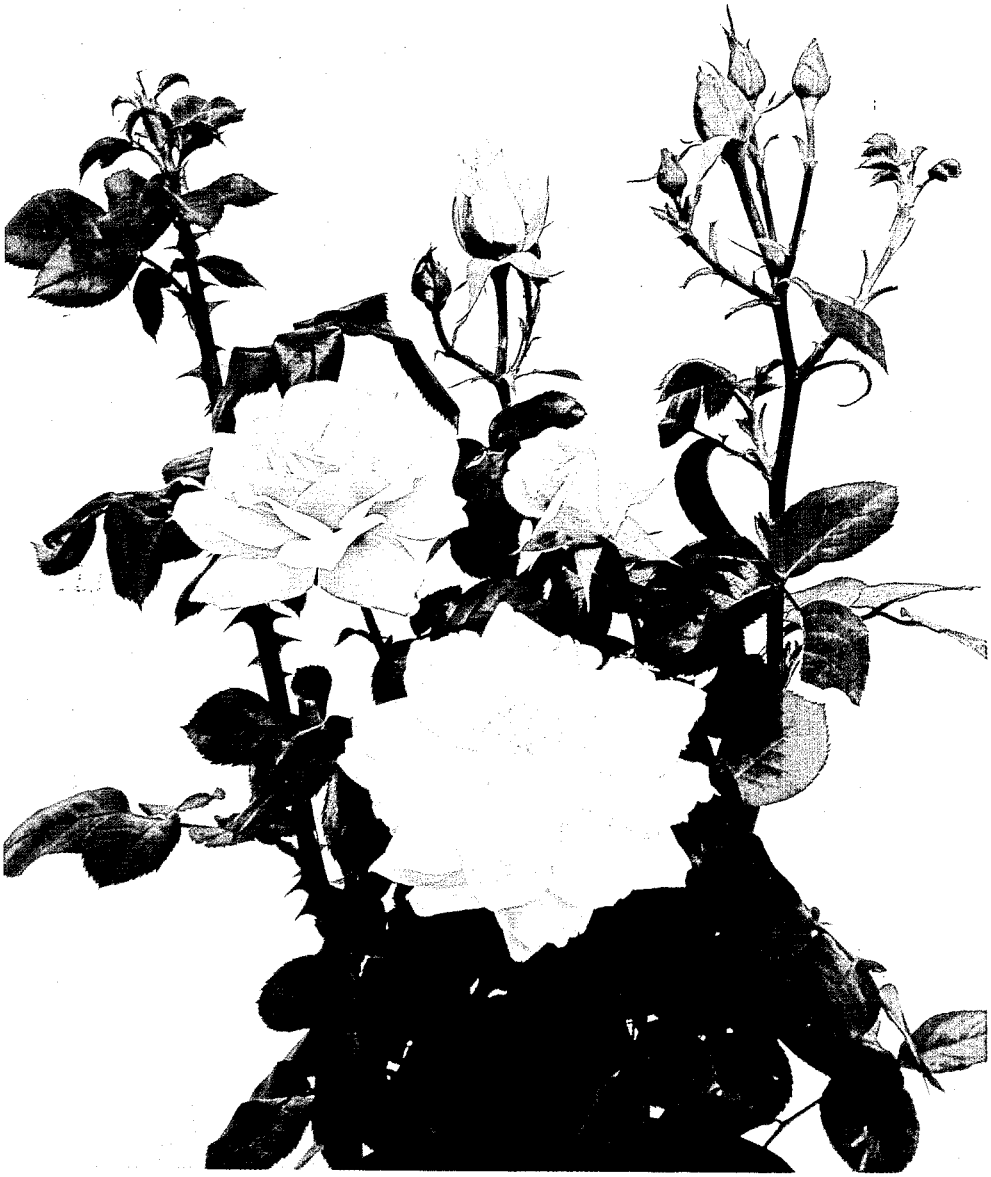

United States Patent Office

Plant Pat. 3,302
Patented Feb. 13, 1973

3,302
ROSE PLANT

David L. Armstrong, Upland, Calif., assignor to Armstrong Nurseries, Inc., Ontario, Calif.

Filed Apr. 15, 1971, Ser. No. 134,514
Int. Cl. A01h 5/00
U.S. Cl. Plt.—27 1 Claim

ABSTRACT OF THE DISCLOSURE

A floribunda rose of spreading and vigorous bushy growth, abundantly covered with medium-sized somewhat leathery and semi-glossy leaves, having peduncles of short to average length which are smooth except for numerous stipitate glands, the flower of said floribunda rose being characterized in that even from the opening of the bud the petals have pronounced apexes that are from acute to acuminate, seen especially on the outside and intermediate petals. The petalage of the freshly opened flower is double, comprising up to 45 petals and 10 to 14 petaloids in a bloom measuring more than 3 inches but less than 4 inches in diameter. The coloration of the flower is predominantly medium salmon-pink.

This invention relates to a new rose plant of the floribunda class. The plant is a seedling of the outdoor bush type, cultivated for cut flowers and for garden decoration. It was propagated by David L. Armstrong in Ontario, California, having as its seed parent "Sumatra" (Plant Patent No. 1,572) and, as its pollen parent, "Circus" (Plant Patent No. 1,382). It holds its distinguishing characteristics through succeeding propagations by budding.

The new variety bears its flowers usually two to five, or more, in regular clusters, on normal short to medium-length stems. Sometimes, however, the flowers are borne singly. The plant blooms abundantly outdoors, and nearly continuously during the growing season. The bloom has a slight to moderate tea fragrance.

Among the differences between this new variety of rose plant and its seed parent, Sumatra, the following may be noted:

Although the plants of both offspring and parent are relatively spreading, the new variety is substantially taller and more floriferous than its seed parent, Sumatra, in plant size and habit.

This new variety has flowers popularly described as medium salmon-pink, whereas the flowers of its seed parent, Sumatra, would be described as signal-red.

The flowers of this new variety have from 35 to 45 petals, plus a number of additional petaloids, whereas the flowers of Sumatra have only 23 to 28 petals.

Among the differences between this new variety of rose plant and its pollen parent, Circus, the following may be noted:

This new variety of plant is distinctly spreading in habit, whereas the plant of Circus is essentially upright.

The semi-glossy leaves of this new variety are lighter green and of a somewhat more grayed hue than the leaves of Circus, which are very dark green and are glossy in surface appearance.

This new variety has peduncles which are characterized by numerous slender stipitate glands, but with no prickles, while the peduncles of Circus have both gland tipped cilia and prickles.

Whereas the bud and opening flower of this new variety are accentuated by acute to acuminate apexes of the petals, the petals of the Circus flower have no such pointed apex, their most prominent characteristic being a reflexing which gives the bud a definite urn shape.

The general color effect of flowers of this new variety is, as noted, medium salmon-pink, whereas the flowers of its pollen parent, Circus, would popularly be described as yellow marked pink, salmon and scarlet.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

*Bud*

The peduncle is short to average length and of average caliper, erect, and smooth except for numerous stipitate glands. The color is near Strong Yellow Green, 5GY 6/8, overlaid with near Dark Red, 5R 3/7.

Before the calyx breaks, the bud is small to medium in size, of moderately short to medium-length, and usually pointed to ovoid in form.

As the calyx breaks, the color is between Strong Red, 5R 4/12, and Dark Reddish Orange, 7.5R 4/11.

The inner surface of the sepals carries a fine tomentum. The margins of alternate sepals are lined with fine tomentum; margins of others usually have small foliaceous appendages. The tips of the sepals usually have very small foliaceous appendages.

On their outer surfaces the sepals have small stipitate glands.

As the first petal opens, it is small, short to medium-length, and ovoid. The color on the outside of the petal is between Strong Purplish Pink, 7.5RP 7/10, and Deep Pink, 10RP 6/12. The color on the inside of the petal is near Deep Pink, 10RP 6/12. The bud opens up well, and is not retarded or prevented from opening by cold, hot, wet, or dry weather.

*Bloom*

When fully open, the bloom is average in size, being from 3¼ inches to 3¾ inches. The petalage is double, with from about 35 to 45 petals and usually with from 10 to 14 petaloids arranged irregularly. The bloom is full and high centered at first, with petals somewhat tightly cupped, with tips rolled outward. Later, at maturity, the petals become more loosely cupped, with tips rolled outward.

The petals are of medium thickness, very slightly leathery, the inside slightly satiny to velvety and the outside shiny to satiny. The outside petals are somewhat broadly obovate, with apex acute to acuminate. The intermediate petals are obovate, with apex acuminate and sometimes having one notch. The inside petals are obovate, sometimes irregularly scalloped, and usually with one notch. The colors may be modified by being shaded and/or washed with other colors.

The paragraphs immediately following describe color values observed in a flower newly opened in the month of September. The plant had been grown outdoors, in Ontario, Calif.

The outer surface of the outside petal was between Light Purplish Pink, 5RP 8/5, and Strong Purplish Pink, 7.5RP 7/10. The inner surface of the outside petal was between Strong Purplish Pink, 7.5RP 7/10, and Strong Pink, 10RP 7/8.

The outer surface of the intermediate petal was near Strong Purplish Pink, 7.5RP 7/10. The inner surface of the intermediate petal was between Strong Purplish Pink, 7.5RP 7/10, and Deep Pink, 10RP 6/12.

The outer surface of the inner petal was between Strong Purplish Pink, 7.5RP 7/10, and Strong Pink, 10RP 7/8. The inner surface of the inner petal was between Strong Pink, 10RP 7/8, and Deep Pink, 10RP 6/12.

The paragraphs immediately following describe the color values observed in a bloom which had been open for three days, outdoors, in the month of September. The plant had been grown outdoors, in Ontario, Calif.

The outer surface of the outside petal was between Light Purplish Pink, 5RP 8/5, and Light Purplish Pink, 7.5RP 8/5. The inner surface of the outside petal was between Strong Purplish Pink, 7.5RP 7/10, and Moderate Pink, 10RP 8/5.

The outer surface of the inner petal was between Light Purplish Pink, 7.5RP 8/5, and Strong Purplish Pink, 7.5RP 7/10. The inner surface of the inner petal was near Strong Pink, 10RP 7/8.

The general color effect of the newly opened flower is near Deep Pink, 10RP 6/12. The bloom after being three days open gives a general color effect between Strong Purplish Pink, 7.5RP 7/10, and Strong Pink, 10RP 7/8. The petals usually drop off cleanly, except for some petaloids. They are not particularly affected in this respect by cold, hot, wet, or dry weather.

The flower on the bush in the garden, in Ontario, Calif., persists from 3 to 5 days in the month of November. Cut roses grown outdoors and kept at living-room temperatures last up to five days in the month of November.

*Reproductive organs*

Stamens: There are many stamens, regularly arranged about the pistils, a few being mixed with petaloids.

Filaments: The filaments are short to medium length, being usually from 5 to 8 mm. long, and near Vivid Yellow, 5Y 8/12, at the base, blending to near Strong Yellowish Pink, 10 R 7/9, as it approaches the anther. Most are with anthers.

Anthers: The anthers are medium size and open at various times. On both the upper and lower side the margins are between Vivid Yellow, 2.5Y 8/12, and Moderate Orange Yellow, 10YR 8/10, with the central area being off-white.

Pollen: Pollen is sparse, and near Brilliant Yellow, 2.5Y 9/9, in color.

Pistils: There are many pistils, being approximately 100 in number.

Styles: The styles are moderately uneven, short to average in length (6–10 mm.), average caliper, and bunched. The style is between off-white and Brilliant Yellow, 2.5Y 9/9, but sometimes having streaks near the stigma which are near Vivid Red, 5R 5/13.

Stigma: The stigma is near Brilliant Yellow, 5Y 9/9.

Ovaries: Usually, most of the ovaries are enclosed in the calyx, with a few protruding therefrom.

Hips: The hips are short and globular, but sometimes pear-shaped, smooth, thick and fleshy. The color is near Strong Orange, 2.5YR 6/12, overlaid with between Strong Reddish Orange, 7.5R 5/13, and Strong Reddish Orange, 10R 5/11, on the side exposed to the sunlight.

Sepals: The sepals are permanent, short, and curved back over the hip. The color on the inside is between Moderate Yellowish Brown, 10YR 4/4, and Moderate Olive Brown, 2.5Y 4/4, overlaid in some places with near Olive Gray, 5Y 3/1. The outside is near Strong Yellowish Brown, 10YR 5/5, overlaid with near Light Olive, 5Y 5/6, towards the tip and margins.

Seeds: The seeds are average in number, usually from 6 to 10, and medium-sized.

*Foliage*

The compound leaves usually comprise three to seven leaflets. They are abundant, medium in size, moderately thin to somewhat leathery, and semi-glossy. The leaflets are oval to ovoid, with apex usually acute, base obtuse, and margin simply to doubly serrate.

The mature foliage on its upper surface is between Grayish Olive Green, 5GY 3/2, and Moderate Olive Green, 5GY 4/3. The under surface is between Moderate Yellow Green, 2.5GY 5/5, and Moderate Yellow Green, 5GY, 5/6.

The upper surface of the young foliage is the same coloring as the mature foliage, but is overlaid with near Dark Red, 2.5R 3/7; on its under surface it is between Strong Yellow Green, 7.5GY 6/8, and Strong Yellow Green, 7.5GY 7/9, and overlaid with near Dark Red, 5R 3/7.

The rachis is average in size. The upper side is grooved, with some stipitate glands on the edges. The under side is moderately smooth, with stipitate glands and a few prickles.

The stipules are medium-length, medium-width, and with short to medium-length points which turn out at an angle which is usually less than 90°.

The plant displays an average resistance to mildew, when compared with other varieties now in commerce and grown under comparable conditions at Ontario, Calif.

*Growth*

The plant is low, bushy, and spreading in habit, and much branched. It displays a moderately vigorous growth. The canes are of medium caliper.

The main stems are between Moderate Olive Green, 5GY 4/3, and Moderate Yellow Green, 5GY 5/6, in color. Thy bear few to several large prickles, which are medium-length, usually hooked slightly downward, with medium-length narrow base. There are several small prickles, and both the large prickles and the small prickles are near Strong Brown, 5YR 4/5, in color. There are no hairs.

The branches are between Moderate Olive Green, 2.5GY 4/3, and Moderate Yellow Green, 2.5GY 5/5, in color. There are few to several large prickles of medium length, hooked slightly downward, with short to medium-length base. Their color is between Strong Brown, 5YR 4/5, and Moderate Brown, 7.5YR 4/5. There are few to several small prickles, and these are the same color as the large prickles. There are no hairs.

The new shoots are near Moderate Yellow Green, 5GY 5/6, or Strong Yellow Green, 5GY 6/8, overlaid with near Moderate Reddish Brown, 10R 3/4, on the sides exposed to sunlight. There are few large prickles, and these are short to medium-length, hooked slightly downward, with medium-length base. Their color is near Dark Red, 2.5R 3/7. There are few to several small prickles. There are no hairs, but sometimes these new shoots have a few to many small stipitate glands.

I claim:

1. A bushy, vigorous rose plant of the floribunda class, substantially as herein shown and described, and distinguished by a plurality of the following features in combination: its spreading habit of growth, the abundance of its semi-glossy foliage, the smoothness of its peduncles, except for stipitate glands; the characteristic appearance of numerous intermediate and outer petals of the flower, with acute to acuminate apexes; the abundance of the pistils and the medium salmon-pink effect of the flower coloration.

No references cited.

ROBERT E. BAGWILL, Primary Examiner